United States Patent [19]

Watanabe et al.

[11] Patent Number: 4,831,020

[45] Date of Patent: May 16, 1989

[54] INGREDIENT EFFECTIVE FOR ACTIVATING IMMUNITY OBTAINED FROM *CHLORELLA MINUTISSIMA*

[75] Inventors: Souichirou Watanabe, Tokyo; Akira Seto, Kanagawa, both of Japan

[73] Assignee: The Nisshin Oil Mills, Ltd., Tokyo, Japan

[21] Appl. No.: 777,169

[22] Filed: Sep. 18, 1985

[30] Foreign Application Priority Data

Sep. 26, 1984 [JP] Japan ................................ 59-199412

[51] Int. Cl.$^4$ ..................... A01N 31/00; A61K 31/70; C08B 37/00; C12R 1/89
[52] U.S. Cl. ..................................... 514/54; 514/885; 536/123; 435/946
[58] Field of Search .................. 514/54, 885; 536/123; 435/946

[56] References Cited

U.S. PATENT DOCUMENTS

| 3,939,279 | 2/1976 | Kawano et al. | 435/946 |
| 4,254,257 | 3/1981 | Schroeck | 536/55.1 |
| 4,533,548 | 8/1985 | Umezawa et al. | 514/54 |

FOREIGN PATENT DOCUMENTS 43-16046  7/1968  Japan ...................................... 514/54

OTHER PUBLICATIONS

Kojima, M. et al.; Chemical Abstracts vol. 78 p. 178 39710s (1973).
Kojima, M. et al; Chemical Abstracts vol. 79 p. 291 90383k (1973).

*Primary Examiner*—Ronald W. Griffin
*Assistant Examiner*—Nancy S. Carson
*Attorney, Agent, or Firm*—Kane, Dalsimer, Sullivan, Kurucz, Levy, Eisele & Richard

[57] ABSTRACT

An ingredient for activating immunity more effective than that obtained from limnetic chlorella is provided, which ingredient comprises polysaccharide contained in marine chlorella as an active ingredient, and which is obtained by dissolving an extract of a marine chlorella with hot water in an alcohol, removing an alcohol-soluble matter from the extract and further removing a low molecular weight substance from the resulting extract by means of gel-filtration or the like.

3 Claims, No Drawings

INGREDIENT EFFECTIVE FOR ACTIVATING IMMUNITY OBTAINED FROM *CHLORELLA MINUTISSIMA*

BACKGROUND OF THE INVENTION

1. Field of the Invention

This invention relates to an ingredient effective for activating immunity, obtained from marine Chlorella.

2. Related Art Statement

A number of substances effective for activating immunity have so far been reported and many of these substances are those contained in bacteria, fungus body component, fungi, etc. Further it has been clarified that a fraction extracted from limnetic Chlorella and containing polysaccharide, too has a similar effect (Japanese patent application laid-open No. Sho 58-15920/1983). Still further it has been confirmed that a substance effective for activating immunity is also present in oyster as a marine living (Proc. Symp. WA-KAN-YAKU 15 (1982) 192–198). Whereas, pharmacologic effects of marine microorganisms have not yet been studied so much up to the present.

SUMMARY OF THE INVENTION

The present inventors have made extensive research in order to search for a substance effective for activating immunity from among marine microorganisms, and as a result have found that a polysaccharide ingredient contained in marine Chlorella has a more extense effect for activating immunity than that of limnetic Chlorella.

The present invention resides in an ingredient for activating immunity comprising polysaccharide contained in marine Chlorella as an active ingredient.

DETAILED DESCRIPTION OF THE INVENTION

The marine Chlorella referred to in this invention is not limited to particular species and genuses, but usually refers to those classified into *Chlorella minutissima*, *Chlorella vulgaris* or the like. The above ingredient effective for activating immunity may be obtained for example as follows, but the present invention should not be construed to be limited thereto:

To powder of a marine Chlorella is added water in a quantity of 5 to 10 times the weight of the powder, followed by heating the mixture to 80° and 100° C. for 30 minutes and then filtering off to obtain a hot water-extract, to which adding ethanol, standing for one hour, washing, filtering, collecting precipitates, dissolving them in a small quantity of water, subjecting the solution to gel-filtration with Sephadex G-50 ®, to remove a low molecular weight substance, collecting the resulting high molecular weight fractions and freeze-drying these to obtain a sample. The resulting high molecular weight fractions contain the aimed polysaccharide contained in the marine Chlorella.

As for the method for judging the effect of immunity activation, there are those directed to limphocyte mitogenic activity, antibody production-reinforcing activity and carbon clearance performance-raising activity, and the present inventors examined the immunity-activating effect of the above sample employing the antibody production-reinforcing activity in mouse spleen as its indication. As a result the effect has been confirmed and further we examined its tumor-resistant effect, too, by way of an in vivo system.

In examining the tumor growth-inhibiting effect, the growth-inhibiting effect on various tumor cells has been examined up to the present, and its tumor-resistant activity in mouse tumor Sarcoma 180 has now been confirmed.

As a result of the above examination, the immunity-activating effect has been confirmed with the above ingredient obtained from the marine Chlorella. Thus, it has been exhibited that tumor-resistant effect and prevention of infection of viruses such as influenza can be expected.

EXAMPLE 1

A marine Chlorella (*Chlorella minutissima*) and a limnetic Chlorella (*Chlorella regularis*) were each examined. Ten liters of water was added to and mixed with 1 kg of powder of each of the Chlorellas, and the mixture was heat treated at 80° and 100° C. for 30 minutes, followed by filtering off to remove cell residue, freeze-drying the resulting supernatant to obtain powder, dissolving the powder in small quantity of water, dissolving the solution in 95% ethanol to 80% (v/v) concentration, refluxing the mixture for 2 hours to dissolve impurities in ethanol, filtering off the ethanol solution, dissolving the resulting ethanol-insoluble matter in a small quantity of water, feeding a portion of the resulting aqueous solution (solids content: 1 g) to a column (2.0 cm$\phi$ × 50 cm) filled with Sephadex G-50 ® (sufficiently washed with water in advance and filled) to carry out gel-filtration, employing water or 0.1M phosphate buffer as an eluting solvent, taking a portion of the resulting respective fractions to determine the content of ethanol-precipitate, collecting fractions rich in ethanol-precipitate to remove most of a low molecular weight substance, and freeze-drying the fractions in the form of solution to obtain a substance composed mainly of polysaccharide.

The product from the marine Chlorella will hereinafter be referred to as sample A and that from the liminetic Chlorella, as sample B.

Next, using the dry powder, the antibody productivity-promoting activity was examined.

Using ICR mice (6-weeks-aged male 10 mice every group), $1 \times 10^8$ sheep erythrocites per one mouse were intravenously injected to immunize them. At the same time, sample A or sample B in quantities indicated later was administered into their peritoneum. After 4 days, the antibody productivity (PFC activity) of mouse spleen lymphocyte against sheep erythrocyte was measured. The results are shown in Table 1.

As seen in the Table, when 30 mg/kg or more of sample A was administered, increase in the antibody productivity as an indication of the immunity activation phenomenon was confirmed. Further, in comparison of the results of sample A with those of sample B, the effect of sample A was clearly confirmed to be more intense than that of sample B.

EXAMPLE 2

Using samples A and B of Example 1, tumor-resistance in vivo was examined.

Tumor cells (Sarcoma 180) subjected to subculture in a manner of ascitic fluid culture were suspended in physiological saline and the resulting suspension was implanted into the inquinal region, intracutaneously, of ICR mice in a quantity of $5 \times 10^6$ cells per one mouse. At the same time of the implant, samples A and B each in quantities indicated below were administered continuously for 10 days into the peritoneum. Four weeks after the implant of the tumor cells, tumor was removed from the mice to measure its weight. The results are shown in Table 2.

From the results, a more intense tumor growth-inhibiting effect was confirmed with sample A than with sample B.

TABLE 1

| | PFC Activity | | | |
| --- | --- | --- | --- | --- |
| | Amount administered | | | |
| Sample | Not administered | 150 (mg/kg) | 30 (mg/kg) | 1 (mg/kg) |
| A | 15 ± 0.5 | 250 ± 25 | 145 ± 38 | 27 ± 0.9 |
| B | 15 ± 0.5 | 120 ± 25 | 80 ± 19 | 18 ± 0.6 |

TABLE 2

| | Tumor Weight | | | | |
| --- | --- | --- | --- | --- | --- |
| | Amount administered | | | | |
| Sample | Not administered | 150 (mg/kg) | 100 (mg/kg) | 50 (mg/kg) | 10 (mg/kg) |
| A | 5.8 ± 0.9 | 2.5 ± 0.3 | 2.8 ± 0.3 | 4.0 ± 1.2 | 6.1 ± 1.0 |
| B | 5.8 ± 0.9 | 4.0 ± 0.8 | 4.8 ± 1.1 | 5.2 ± 1.8 | 6.0 ± 0.9 |

What we claim is:
1. A composition having immuno-stimulating activity comprising as an active ingredient polysaccharide derived from marine *Chlorella minutissima*.
2. A composition having immuno-stimulating activity according to claim 1 wherein said polysaccharide is a product obtained by preparing an extract of a marine Chlorella with a small quantity of hot water, dissolving the extract in an 80 percent (v/v) concentration of alcohol and removing by gel filtration a low molecular weight substance from the resulting insoluble matter, thereby obtaining high molecular weight fractions.
3. A composition having immuno-stimulating activity of claim 2 wherein said alcohol is ethanol.

* * * * *